United States Patent
Beerens et al.

(10) Patent No.: US 9,744,042 B2
(45) Date of Patent: Aug. 29, 2017

(54) CRANIAL IMPLANT

(75) Inventors: Maikel Michael Adrianus Beerens, Maastricht (NL); Paul Frans Jozef Laeven, Vijlen (NL); Jules Maria Nikolaas Poukens, Elen-Bilsen (BE)

(73) Assignee: ACADEMISH ZIEKENHUIS MAASTRICHT; UNIVERSITEIT MAASTRICHT, Maastricht (NL)

( * ) Notice: Subject to any disclaimer, the term of this patent is extended or adjusted under 35 U.S.C. 154(b) by 300 days.

(21) Appl. No.: 13/497,532

(22) PCT Filed: Sep. 21, 2010

(86) PCT No.: PCT/EP2010/063887
§ 371 (c)(1),
(2), (4) Date: Apr. 27, 2012

(87) PCT Pub. No.: WO2011/036148
PCT Pub. Date: Mar. 31, 2011

(65) Prior Publication Data
US 2012/0203289 A1     Aug. 9, 2012

(51) Int. Cl.
*A61B 17/80* (2006.01)
*A61F 2/28* (2006.01)
(Continued)

(52) U.S. Cl.
CPC .......... *A61F 2/2875* (2013.01); *A61B 17/17* (2013.01); *A61B 17/1739* (2013.01); *A61B 17/86* (2013.01);
(Continued)

(58) Field of Classification Search
CPC .. A61B 17/8061; A61B 17/688; A61F 2/2803
(Continued)

(56) References Cited

U.S. PATENT DOCUMENTS 4,388,921 A * 6/1983 Sutter et al. .................. 606/71
5,201,737 A * 4/1993 Leibinger ............ A61B 17/688
606/280
(Continued)

FOREIGN PATENT DOCUMENTS

DE     10205912     8/2003
EP     1099416     5/2001
(Continued)

OTHER PUBLICATIONS

International Search Report, mailed Jan. 21, 2011 in connection with International Patent Application No. PCT/EP2010/063887.
(Continued)

*Primary Examiner* — Todd E Manahan
*Assistant Examiner* — Jessica Weiss
(74) *Attorney, Agent, or Firm* — Steven M. Koehler; Westman, Champlin & Koehler, P.A.

(57) ABSTRACT

An implant, such as a cranial implant, for attachment to a defect in a bone structure having an edge is described. The implant comprises a direction of extension and a rim extending substantially perpendicular to the direction of extension of the implant. The rim is configured to be attached to the edge of the bone structure and comprises at least one mounting portion (6) configured to accommodate a fastener such that at least a portion of the fastener is extendible in a direction extending away from the rim at an angle which is at most acute with respect to the direction of extension of the implant. The implant is configured such that upon placing the implant in the defect, the fastener is extendible into the edge of the bone defect in a controllable manner.

19 Claims, 3 Drawing Sheets

(51) Int. Cl.
*A61B 17/17* (2006.01)
*A61B 17/86* (2006.01)
*A61F 2/30* (2006.01)

(52) U.S. Cl.
CPC ............... *A61F 2002/30774* (2013.01); *A61F 2002/30787* (2013.01); *A61F 2002/30794* (2013.01); *A61F 2002/30948* (2013.01); *A61F 2310/00023* (2013.01); *A61F 2310/00179* (2013.01)

(58) Field of Classification Search
USPC ...... 606/902–906, 70–71, 280–299, 74, 323, 606/86 B, 86 R, 87, 96; 623/17.19
See application file for complete search history.

(56) References Cited

U.S. PATENT DOCUMENTS

| | | | |
|---|---|---|---|
| 5,501,685 A | | 3/1996 | Spetzler |
| 5,569,250 A | * | 10/1996 | Sarver et al. ................. 606/281 |
| 5,669,912 A | * | 9/1997 | Spetzler ......................... 606/916 |
| 6,179,839 B1 | * | 1/2001 | Weiss ................. A61B 17/1659 606/280 |
| 6,197,030 B1 | | 3/2001 | Pham |
| RE37,249 E | * | 6/2001 | Leibinger ............ A61B 17/688 606/280 |
| 6,379,363 B1 | * | 4/2002 | Herrington .......... A61B 17/688 606/104 |
| 6,537,277 B2 | * | 3/2003 | Vom Berg et al. ............. 606/71 |
| 6,618,623 B1 | | 9/2003 | Pless et al. |
| 7,189,237 B2 | * | 3/2007 | Huebner ............ A61B 17/1728 606/291 |
| 2006/0224242 A1 | * | 10/2006 | Swords et al. ............. 623/17.19 |

FOREIGN PATENT DOCUMENTS

| | | |
|---|---|---|
| EP | 2014258 | 1/2009 |
| EP | 2014258 A1 * | 1/2009 |
| GB | 2379185 | 3/2003 |
| WO | 2005074580 | 8/2005 |

OTHER PUBLICATIONS

Machine translation of DE 10205912.
State Intellectual Property Office of the People's Republic of China in corresponding Chinese Application No. 201080050794.2, date of notification Mar. 4, 2014.

* cited by examiner

CRANIAL IMPLANT

PRIORITY CLAIM TO RELATED APPLICATIONS

This application is a national stage application under 35 U.S.C. §371 of PCT/EP2010/063887, filed Sep. 21, 2010, published as WO 2011/036148 A1 on Mar. 31, 2011, and claiming priority to European Application No. 09171189.5, filed Sep. 24, 2009, which both International and European applications and publications are incorporated herein by reference and made a part hereof in its entirety, and the benefit of priority of which is claimed herein.

The present disclosure relates to an implant, such as a cranial implant, for attachment to an edge of a defect in a bone structure, the implant comprising a direction of extension at or near the rim extending substantially perpendicular to the rim wherein the rim is configured to be attached to the edge of the bone structure.

Such implants, which are sometimes referred to as patient specific implants (PSI), are employed for repairing defects in bone structures resulting from e.g. surgery or trauma and/or a birth defect. An implant partially or fully closes a defect, such an opening in a skull, protects the tissue underneath, e.g. brain tissue, and/or corrects and/or restores the contour of the bone structure. Such implants are generally custom made, preferably adhering to the ISO 13485 quality management standard for medical devices.

Implants may have different origins. For instance, autogenous grafts are taken from one part of a human or animal body and implanted in another part of that same body and allografts are bone grafts taken from an individual from a species and inserted in the body of another individual of that same species. Alloplastic implants are implants made from body foreign material.

All implants have in common that they must be securely fixed to the bone structure. Implant migration and micro-movements may hinder osteointegration (sometimes also referred to as osseointegration) and even result in rejection of the implant. Implant fixation is generally done by suturing or screwing the implant to the bone structure via holes, which are provided into or through the implant and/or the bone structure.

U.S. Pat. No. 6,618,623 discloses a ferrule for retaining an implantable device within a cranial opening of a patient. The ferrule is inserted into the cranial opening and fixed to the cranium. Then an implantable device is inserted into the ferrule and secured thereto. The ferrule may comprise an intra-osseous extension and is secured to the patient's cranium with (self-tapping) bone screws.

EP 2 014 258 by the present inventors pertains to an implant, such as a cranial implant, comprising a rim and one or more fasteners for attaching the rim to an edge of a defect in a bone structure. One side of the rim is broader than the other side of the rim and/or comprises one or more protrusions extending beyond the periphery of the other side of the rim, such that, upon placing the implant in the defect, the rim and/or protrusions rest(s) on the edge of the defect. The fastener(s) is/are mounted or mountable in or on at least the rim and comprise(s) at least one element which is extendible in a direction away from the rim to grip underneath the bone structure. The fasteners of the implant of EP 2 014 258 are accommodated in clip mounts or guides configured such that a portion of the fastener is extendible in a direction extending away from the rim at an angle which is at most acute with respect to the direction of extension of the implant, so as to be extendible underneath the bone structure.

U.S. Pat. No. 6,197,030 discloses elastic-loaded retractable shank surgical pins having a hollow shank adapted to receive an elastic-loaded retractable shank which can be inserted into a bone flap or into the walls of a skull cavity from which the bone flap has been removed, when the retractable shank is compressed against the elastic loading, and the bone flap is placed into position in the skull cavity. The retractable shanks are allowed to expand outwards into corresponding holes positioned in the skull or bone flap, securing the latter in place without the necessity of protruding wires or other conventional locating devices. The pins need not be positioned parallel to each other, and may be spaced around the bone flap, preferably constituting the sole means of securing the bone flap in the skull cavity. However, such pin type devices are relatively complex and therefore expensive and delicate devices, in particular relative to a screw. Such pin type devices also do not allow removal of the bone flap once implanted, e.g. in case of complications. Relying on elastic loading, the pins cause compressive forces onto the skull and/or the bone flap which cannot be determined and/or controlled accurately and micro-movements of the pin and/or the bone flap with respect to the skull are inherent.

Bone screws, tacks and the like are proven techniques but necessitate intrusion into the bone structure and, once applied, exert (lateral) compressive forces on the bone structure. Compressive forces in turn may cause resorption of bone and loosening of the fixing means. Micro-movements due to play between different parts of the implant or the fixing means or between the fixing means and the bone structure and/or implant may increase damage and loosening and should be prevented. A balance should thus be found between minimum compressive forces and optimum fixation. Further, the implant and its fixation means form an invasive volume inside the patient's body. Such volume should be minimal, in particular for a cranial implant to prevent damage to the brain.

It is an object of the present disclosure to provide an improved implant.

To that end, the implant according to the present disclosure is characterised in that the implant is configured such that upon placing the implant in the defect, the fastener is extendible into the edge of the bone defect in a controllable manner.

In one aspect, the at least one mounting portion is configured such that upon placing the implant in a defect in a curved bone structure having a curvature at or near the edge, e.g. a convex shape, the extendible portion of the fastener is extendible in a direction which is substantially tangential to the curvature of the bone structure at or near the edge at or near the mounting portion. Thus, the direction of the fastener conforms to the anatomic shape of the bone structure.

In another aspect, the implant has a curved shape, such as a convex shape, having a curvature at or near the rim and the at least one mounting portion is configured such that at least the extendible portion of the fastener is extendible in a direction which is substantially tangential to the shape of the implant at or near the rim.

Advantageously, the rim of the implant has a first thickness at the position of the at least one mounting portion and the at least one mounting portion is configured such that the extendible portion of the fastener is extendible from the rim at about the middle of the first thickness.

The implant may be configured for being attached to a bone structure having at least a portion of an edge with a second thickness, wherein the at least one mounting portion is configured such that the extendible portion of the fastener is extendible from the rim at about the middle of the second thickness. Thus, the fastener is extendible into the middle of the (anatomical) shape of the edge of the bone structure, improving achieving of substantially symmetric distribution of any forces with respect to the fastener.

The at least one mounting portions may comprise an enclosed channel.

Advantageously one side of the rim may be broader than the other side of the rim and/or may comprise one or more protrusions extending beyond the periphery of the other side of the rim, such that, upon placing the implant in the defect, the rim and/or protrusions rest(s) on the edge of the defect.

The mounting portion may be configured to receive at least a portion of a guide for a cutter for cutting a recess in the edge of the bone defect.

In a further aspect the implant has a thickness, and the fastener and the at least one mounting portion are configured to define at least one relative position of the fastener and the at least one mounting portion such that one portion of the fastener extends from the implant and a remaining portion of the fastener is accommodated within the thickness of the implant.

At least one fastener may be movably attached to the at least one mounting portion.

Yet another aspect of the present disclosure is a kit of parts comprising an implant as described herein and one of one or more fasteners, one or more guides for guiding a cutter, one or more cutters and/or tools for operating a fastener.

The at least one mounting portion may have a first shape with the guide having a shape complementary to the first shape.

The present implant allows fixing the implant to the defect with improved accuracy and safety. The implant further allows fixation such that the implant remains in position and fixed also when the holding force between the fastener and the implant is reduced, e.g. by the fastener becoming loose within the bone structure edge. The implant may be custom made pre-operatively and fixed in place with mounting portions at predetermined positions in a relatively faster and more secure way than prior art implants.

In some embodiments, the fixing of the implant is reversible such that the implant may be removable if complications, e.g. bleeding, occur.

In another aspect a method of attaching an implant in a defect in a bone structure is provided. The method comprises the steps of providing an implant for attachment to an edge (4) of the defect. The implant comprises a rim and a direction of extension at or near the rim extending substantially perpendicular to the rim. The method further comprises attaching the rim to the edge of the bone structure by extending a fastener in a direction extending away from the rim at an angle which is at most acute with respect to the direction of extension of the implant and into the edge of the bone defect.

The implant may advantageously be prepared pre-operatively, e.g. on the basis of CT-scan data of (the shape of) at least a portion of the defect.

For expediting healing and/or reducing chances of complications, a first shape of at least a portion of the defect may be determined, e.g. via one or more X-ray or CT scan images, and at least a portion of the implant may be formed with a second shape which is substantially complementary to the first shape.

The implant and/or the bone structure may be curved, having a curvature at or near the edge or the rim, respectively, e.g. a convex shape. Then the fastener may be extended in a direction which is substantially tangential to said curvature of the bone structure and/or the implant, respectively.

The implant may be provided with a mounting portion configured to accommodate a fastener, such that at least a portion of the fastener is extendible in a direction extending away from the rim at an angle which is at most acute with respect to the direction of extension of the implant and into the edge of the bone defect. Then a guide may be provided for a cutter for cutting a recess in the edge of the defect, arranging at least a portion of the guide in the at least one mounting portion, and cutting, guided by the guide, a recess for accommodating at least a portion of the fastener into the edge of the defect.

The disclosure will now be explained in more detail with reference to the figures, which show an embodiment and details of the present implant by way of example.

It is noted that the drawings are not necessarily to scale and that details that are not required for understanding the present disclosure may have been omitted. The terms "upward", "downward", "below", "above", and the like relate to the embodiments as oriented in the drawings. Further, elements that are at least substantially identical or that perform an at least substantially identical function are denoted by the same numeral.

FIGS. 1-5 schematically show a portion of a bone structure, here a human skull 1, having a defect 2 resulting from surgery or trauma, which defect 2 is closed by means of a first embodiment of a cranial implant 3 according to the present disclosure. The skull 1 and the implant 3 are generally convex, being curved along two substantially perpendicular directions of extension E. Preferably the shape and directions of extension E of the bone structure 1 and the implant 2 are such that a substantially continuous structure is formed. Such implant allows reconstructing the anatomic shape of the intact bone structure. Some other examples of curved bone structures which may be provided with a curved implant are a rib, a shoulder blade, a pelvis. The defect 2 has an edge 4 surrounding the defect 2. In the cross-sectional view of FIGS. 1-4 the edge 4 is rounded indicating that the external and internal laminae cover the diploe and thus that the bone surface has been allowed to heal, typically for two to six months. The edge 4 has a thickness T in a direction substantially perpendicular to the extension E of the bone structure (see FIG. 2), such as here in a substantially radial direction to the convex bone structure of the skull. The implant may be made of a metal, for instance medical grade titanium. Alternative materials include, but are not limited to, polymers, e.g. polymethyl methacrylate (PMMA), polyether ether ketone (PEEK), or polyether ketone ketone (PEKK), and ceramic materials, e.g. zirconium oxide or aluminium oxide. A non-metallic implant 3 tends to remain closer to the local body temperature of the patient than a metallic implant 3, improving comfort and reducing complications. The implant 3 and the rim 5 of the implant 3 can be closely matched to a desired shape and/or to the shape of the edge 4 of the defect 2 by means of CT-scans and 3D modeling, in a manner known in itself, such that a pre-operatively fabricated implant may be employed.

The implant 3 has a rim 5 extending along the implant 3 and directions of extension E of the implant 3 may be defined substantially perpendicular to the rim 5 and following the general curvature of the convex-shaped implant 3. The rim 5 has a thickness t in a direction substantially perpendicular to the extension E of the implant (see FIG. 2), e.g. in a substantially radial direction in the case of a convex implant such as for a cranium. The implant 3 has a generally conical shape in a cross-sectional view with an outward flaring rim, i.e. the side 5A of the rim 5 of the implant 3 facing outwards, i.e. the side that is at least substantially flush with the "lamina externa" of the skull 1, is broader than the side 5B of the rim facing inwards, which rim 5B is at least substantially flush with the "lamina interna". Upon placing the implant 3 in the defect 2 in the skull 1, the outwards-facing side portion of the rim 5A rests on the edge 4 of the defect 2 and, in view of the close fit of the rim 5 and the edge 4, only one degree of freedom remains, i.e. in a direction opposite to the direction of placing the implant 3. To fix the implant 3 in this remaining direction, the shown embodiment of the present implant 3 comprises, along its rim 5, a plurality, e.g. three, mounting portions 6 configured to accommodate a fastener 7. The implant of FIG. 5 comprises eight mounting portions 6, arranged along the rim 5 with various mutual separations and directions for optimum fixation of the implant 3 with minimum impact on the skull 1. The fastener 7 shown in FIGS. 1-4 is a screw, but any suitable fastener such as a bolt, a pin etc. may be provided. The fastener may comprise or be of the same material as the implant or a different material.

Figure 3:
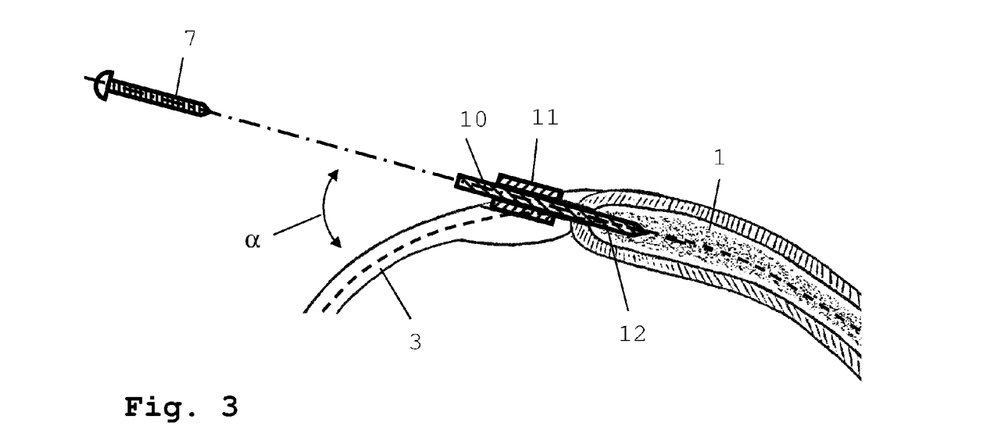
Figure 4:
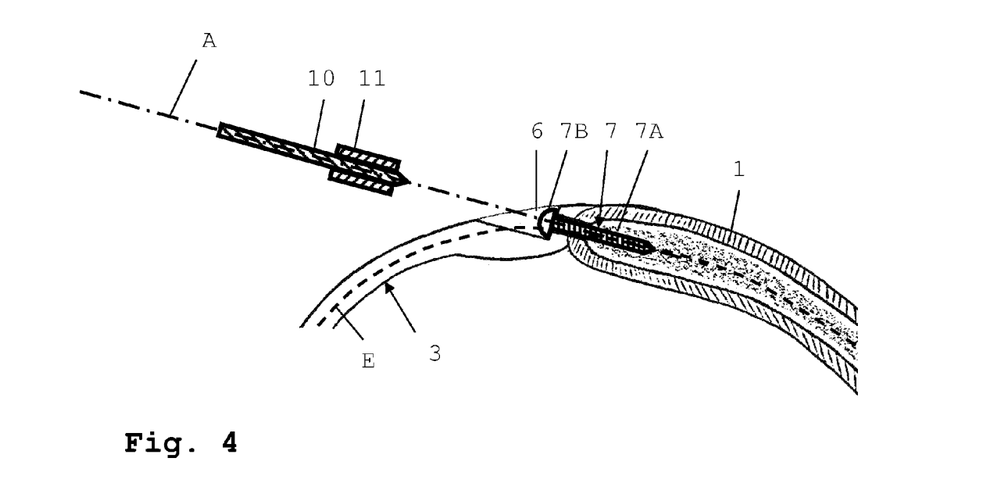
Figure 5:
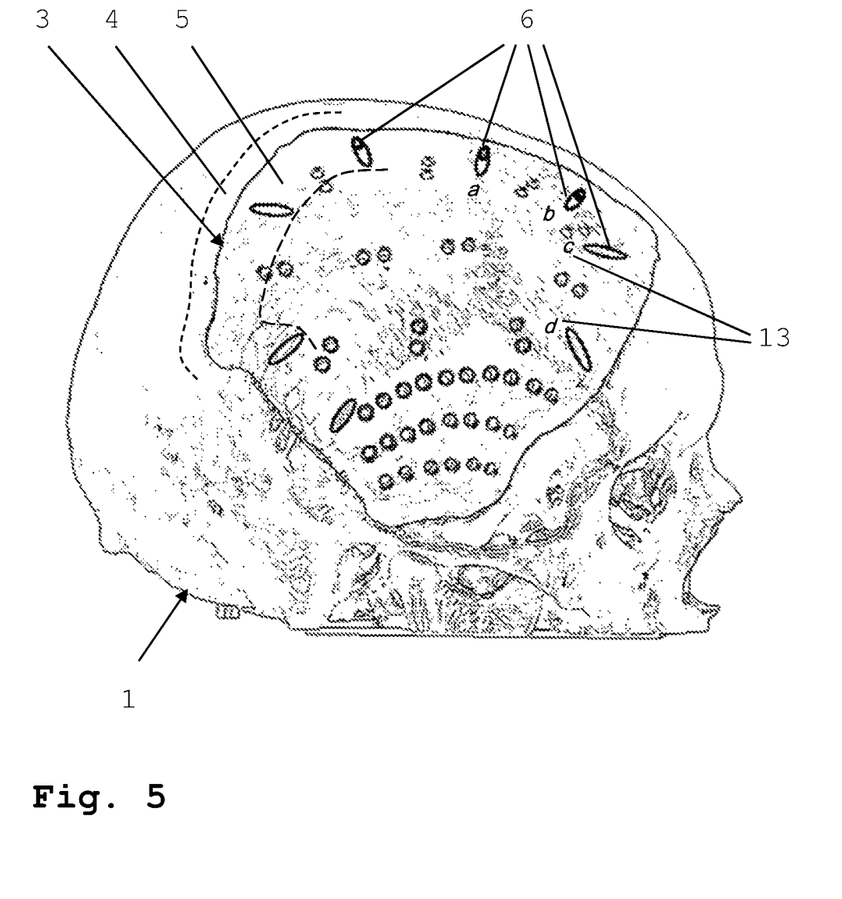
FIG. 5 is a schematic side view of a skull comprising an implant fixed in a defect in the skull.

The shown mounting portion 6 comprises a first channel portion 8 and a second channel portion 9. The first channel portion 8 extends through the material of the implant 3 along an axis A and in the shown embodiment is enclosed by material of the implant 3 perpendicular to the axis A. The second channel portion 9 also extends substantially along to the axis A, is substantially concentric with the channel 8 as seen along the axis A, and is partially enclosed by the implant material, being open towards an exterior side of the implant 3, here in a direction perpendicular to the axis A. A portion of the fastener 7 is accessible from the exterior side of the implant 3 (FIGS. 4, 5). The axis A extends in a direction intersecting the rim 5, generally, but not necessarily, intersecting the rim 5 perpendicularly (e.g. see FIG. 5), and being oriented with respect to the directions of extension of the implant 3 such that the axis A extends at an angle α which is at most acute with respect to the surface and the directions of extension E of the implant 3 at or near the intersection of the axis A with rim 5. The axis A extends at an angle which is at most obtuse with respect to the normal to the implant 3 at or near the intersection of the axis A with rim 5. Determination of the angle α is indicated in FIG. 3 for explanatory purposes only; in the shown embodiments, said direction of extension of the axis A is substantially tangential to the curvatures of both the implant 3 and the skull 1 at the position of the interface between the rim 5 and the edge 4, such that the angle α for the shown embodiments is in fact substantially zero degrees.

The mounting portion 6 is configured such that a portion 7A of the fastener 7 is extendible through the channel 8 from the rim 5 of the implant 3 in a direction along the axis A. E.g., the mounting portion 6 may have a shape complementary to a shape of the fastener 7, such as a screw thread, or by having a larger inner diameter than an outer diameter of the fastener 7.

The mounting portion 6 shown in FIGS. 1-4 is further configured such that the fastener 7 is movably arranged in the rim 5 and a portion 7A is extendible through the mounting portion 6 through the rim 5 in an outwards direction. The extendible portion 7A of the fastener 7 is extendible from the rim 5 at about the middle of the thickness t of the rim 5 and at about the middle of the thickness T of the edge 4, such that the portion 7A of the fastener 7 is arranged substantially symmetrically with respect to the side 5A of the rim facing outwards and the side 5B of the rim facing inwards and similarly symmetrically with respect to sides of the edge 4 facing outwards and inwards, respectively. Thus, the fastener 7, (the rim 5 of) the implant 3 and (the edge 4 of) the bone structure 1 are arranged such that forces between them are exerted substantially symmetrically and localised stresses which might lead to damage and/or complications are prevented.

Figure 1:
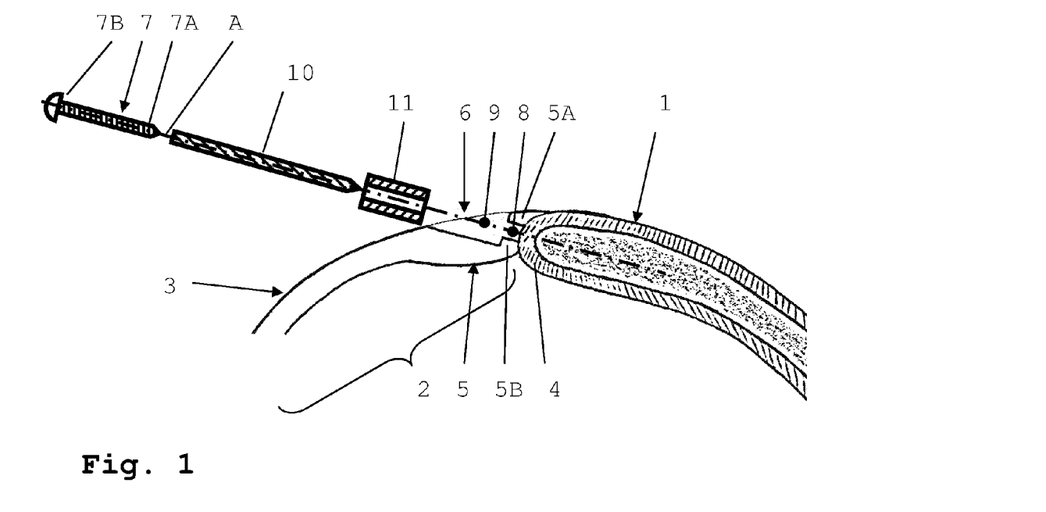
FIGS. 1-4 are schematic partial cross-section views indicating an embodiment of an implant to a portion of a skull and a method of attaching the implant to the skull.

FIG. 1 further shows a portion of a cutter 10, here a drill bit 10, and an optional guide 11 for guiding a direction of operation for the cutter 10.

Figure 2:
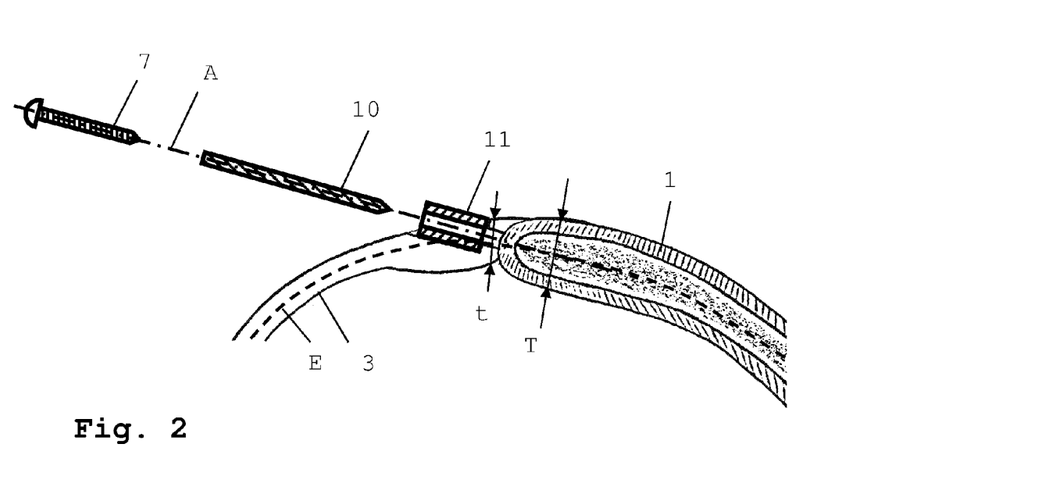

FIGS. 2-4 show attaching the implant 3 to the skull 1. After optional sufficient regeneration of bone material at the edge 4 of the defect 2 in the skull 1, an implant is manufactured to fit at least a portion of the defect 2. The implant 3 may be provided pre-operatively and may be manufactured with one or more mounting portions 6 at predetermined positions on the implant 3. It is also possible, although more cumbersome, to provide mounting portions 6 during the surgical procedure for implantation of the implant 3, e.g. using a dedicated drill bit.

Next, the implant 3 is placed in the defect 2 (FIG. 2). In the shown case, the implant 3 comprises a generally conical shape in a cross-sectional view and the rim 5 of the implant 3 may rest against the edge 4 of the skull 1. This provides a well-defined relative position between the implant 3 and the skull 1.

FIG. 2 further shows the guide 11 for the cutter 10 being arranged in the mounting portion 6 for guiding the cutter 10 in a desired direction, e.g. along the direction of the axis A, and for preventing damage to the material of the implant 3 and/or the mounting portion 6. Contamination of the site of the defect 2 from dust and/or debris from material of the implant 3 may thus be prevented. For further reducing chances of contamination of the site of the defect 2, the guide 11 may be configured for removing debris, e.g. comprising one or more channels and being at least one of connected and connectable to an apparatus for removing debris, such as a suction apparatus. The mounting portion 6 and the guide 11 may have complementary shapes, e.g. one or more plane faces and/or ridges, such that the relative positions of the mounting portion 6 and the guide 11 and the direction of operation of the cutter 10 may be accurately defined.

FIG. 3 shows cutting a recess 12, here drilling a hole 12, into the edge 4 of the skull 1 with the cutter 10 through the guide 11. The direction of extension of the hole 12 is substantially tangential to the curvature of the skull 1, defined by the patients anatomy, such that the hole extends within the bone. Thus, the predetermined position and direction of the mounting portion 6 are transferred to the bone structure 1. In some cases an optimum position of the fastener 7 within the bone structure 1 may be achieved with the fastener 7 extending tangential to a curvature of the bone structure lying at a distance, e.g. approximately 1-5 cm, away from the defect. During planning of the surgery for the implantation, such direction may be accurately determined. The associated mounting portion 6 of the implant 1 may be formed accordingly, so that a fastener 7 inserted via that mounting portion 6 will be positioned in the desired manner and position, determined by the mounting portion 6.

Thereafter, as shown in FIG. 4, the cutter 10 and the guide 11 are withdrawn from the skull 1 and the mounting portion 6, and the fastener 7 is arranged within the mounting portion 6 and into the hole 12 to fix the implant 3 to the skull 1.

The fastener 7 comprises a coupling portion 7B for coupling to a tool, e.g. a transverse slot or a hexagonal feature, for temporarily coupling the fastener with a driver, such as a surgical screwdriver. The fastener 7 is extended into the edge 4 of the skull 1 for a desired distance. The extension of the fastener 7 may be predetermined by the fastener 7 comprising a portion cooperating with a feature of the mounting portion 6. In the shown embodiment, the coupling portion 7A abuts the interface between the first and second channel portions 8, 9. At least at this position, as visible in FIG. 4, one portion 7A of the fastener 7 extends from the implant into the edge 4 of the skull 1 for fastening the implant to the bone structure and the remaining portion of the fastener 7 is accommodated within the thickness of the implant 3, such that it does not protrude from the implant 3 and thus the general contour of the reconstructed bone part, here the combination of skull 1 and implant 3. Thus, chances of the fastener 7 damaging surrounding tissue are minimised and a shallowly implanted implant 3, e.g. an implant 3 substantially only covered by a thin layer of skin tissue such as a cranium, is relatively inconspicuous.

The mounting portion need not comprise a first channel portion 8 and a second channel portion 9 but may be substantially formed as one open channel, possibly having a tapering or a constant size such as an inner diameter. An enclosed channel 8, however, improves strength and accuracy of the mounting portion 6 as well as of the position and direction of the fastener 7 with respect to the mounting portion 6 and thus to (the rim 5 of) the implant 3 and the edge 4 of the bone structure 1.

At a tangential orientation of the fastener 7 with respect to the implant 3 and/or the bone structure 1 there is little or no risk of penetrating fully through the bone and/or damaging underlying tissue while cutting the hole 12 or e.g. the meninges or brain tissue, which is known to happen when screwing a fastener or cutting a hole substantially perpendicular to the bone for fixing a prior art implant by screwing or stitching techniques. Further, the hole 12 can have an extension within the material of the bone structure 1 and/or the implant 3, which is significantly longer than the thickness of the bone structure 1/implant 3, which is a limiting factor for the length of the fastener 7 in the case of perpendicular fastening. This allows increasing the hold of the fastener 7 and reducing chances of the fastener 7 becoming loose. The implant 3 may thus be used with bone structures with relatively little torque strength of the bone material at or near the location of the fastener, e.g. relatively delicate bone structures or bone structures with relatively fresh defect edges that are not (yet) covered with cortical bone. Thus, applicability of the implant is improved.

Further, since the direction of extension of the fastener 7 is different from a direction of detachment of the implant 3 from the skull 1, such as a direction opposite the direction of implantation of the implant 3, the implant 3 remains fixed to the skull 1 also when one or more fasteners 7 inadvertently might become loose or break free from the skull 1. This is in particular the case when plural mounting portions 6 and fasteners 7 are employed, extending in mutually different directions, e.g. several fasteners extending in a substantially radial or star-like pattern with respect to the implant 3.

An implant according to the present disclosure may closely match the shape of (the edge of) the defect and directions of forces exerted on or by the implant with respect to the bone structure may be close to or substantially identical with an intact bone structure.

The implant 3 may comprise one or more markings 13 (see FIG. 5) associated with one or more portions of the implant 3, e.g. mounting portions 6, etc., which may serve as a point of reference and/or to provide information regarding the implant 3, the bone structure 1, etc. The markings may correspond to pre-operatively identified positions and/or constraints to be considered during the implantation operation. E.g., a marking 13 may indicate an orientation of the implant in the defect 2. A marking 13 associated with a mounting portion 6 may indicate one or more dimensions of a fastener 7 to be used with that mounting portion 6, such as the type, length, size and/or diameter of the fastener 7, and/or a force or a torque with which the fastener 7 is to be fastened. Other information may relate to the use of glue or cement etc. A marking 13 may comprise one or more alphanumeric characters or other symbols and may differ or be equal for each marking 13. A marking 13 may comprise the information itself and/or refer to a remote source of information such as a look-up table which may have been prepared in conjunction with designing the implant and/or planning surgery. One or more markings 13 may be substantially permanent e.g. marked with permanent ink, inlaid in, engraved in and/or embossed on the implant, and/or be transient, e.g. marked with removable or resorbable ink or with detachable objects such as stickers. An enclosed channel of a mounting portion 6 may be plugged with an object to be removed during surgery for preventing soiling, damaging and/or clogging of the channel. Such object may carry a marking, e.g. being colour coded.

The time for fixing a pre-operatively prepared implant according to the present disclosure with one or more fasteners, including cutting one or more recesses can be significantly less than prior art fixing methods, in particular compared to methods including casting or modeling an implant during surgery. Time and costs invested in pre-operative determination of desired fixation positions and thus of the position and direction of one or more mounting portions are regained by reduced operation duration. Patient recovery time and chances of complications may also be reduced.

The implant may be provided in a kit together with one or more fasteners, guides for guiding a cutter and/or tooling such as cutters, drills and tools for operating a fastener. A manual and/or lookup-table corresponding to any markings may be provided as well.

The disclosure is not restricted to the above-described embodiments, which can be varied in a number of ways within the scope of the claims. For instance, the mounting portion 6 need not rotationally symmetric, the recess 12 need not be a drilled hole and the fastener need not be an elongated round pin-like object such as a pin or a screw. It is conceivable that the mounting portion and/or the recess is slot-shaped, having a relatively larger size in one direction and a relatively smaller size in another direction perpendicular to a direction of extension, e.g. the direction of penetration into the bone structure of the recess. Such mounting portion and/or recess may be configured to accommodate a blade-like fastener.

It should be noted that (use of) the guide 11 is optional and that a recess 12 may be cut through (the mounting portion 6 of) the implant 3, taking care not to damage the implant 3. A recess 12 may even be cut directly into the edge 4 of the bone structure 1 with or without any further guiding object. Alternatively, the implant 3 may be fixed with self-tapping bone screws, obviating cutting a recess 12, with or without using a guide 11, prior to fixing the implant 3.

An implant 3 may be provided as an integrated assembly with one or more fasteners 7 movably attached to mounting portions 6, such that the fasteners 7 are extendible. In particular when the fasteners are self-tapping bone screws or similar devices such integrated assembly may facilitate a surgical procedure e.g. by preventing dropping or losing a fastener.

Elements and aspects discussed for or in relation with a particular embodiment may be suitably combined with elements and aspects of other embodiments, unless explicitly stated otherwise.

The invention claimed is:

1. An anatomically shaped implant, for attachment to an edge of a defect in a bone structure,
   the implant comprising a central portion and a peripheral rim and the central portion extending from the peripheral rim in a direction of extension, wherein the direction of extension at or near the peripheral rim is substantially perpendicular to a tangential plane along the peripheral rim,
   wherein the peripheral rim is configured to be attached to the edge of the defect in the bone structure and comprises at least one mounting portion in a convex portion of an outwardly facing surface of the peripheral rim when the implant is implanted,
   wherein the at least one mounting portion comprises a channel which is configured to accommodate a fastener such that at least a portion of the fastener is extendible along an axis through the channel and through the peripheral rim, wherein the channel extends along the axis through the peripheral rim, the axis being oriented at an angle which is at most acute with respect to a surface of the implant and the direction of extension of the central portion of the implant at or near the channel, and wherein the axis extends in a direction substantially perpendicular to the tangential plane at or near an intersection of the axis with the peripheral rim,
   wherein the implant is configured such that upon placing the implant in the defect, the central portion covers and closes the defect and the fastener is arranged in the channel and movably with respect to the channel and extendible along the axis into the edge of the bone defect in a controllable manner.

2. The anatomically shaped implant according to claim 1, wherein the at least one mounting portion is configured such that
   upon placing the implant in a bone defect in a curved bone structure having a curvature at or near the edge, the extendible portion of the fastener is extendible along the axis in a direction which is substantially tangential to the curvature of the bone structure at or near the edge at or near the mounting portion so that said extendible portion, when extended, fits within the bone structure.

3. The implant according to claim 2, wherein the curvature has a convex shape.

4. The anatomically shaped implant according to claim 1, wherein the implant has a curved shape having a curvature at or near the peripheral rim and the axis is substantially tangential to the curvature of the implant at or near the peripheral rim such that
   at least the extendible portion of the fastener is extendible in a direction which is substantially tangential to the curvature of the implant at or near the peripheral rim so that said extendible portion, when extended, fits within the bone structure.

5. The anatomically shaped implant according to claim 1, wherein the peripheral rim of the implant has a first thickness at a position of the at least one mounting portion and wherein the at least one mounting portion is configured such that the extendible portion of the fastener is extendible from the peripheral rim at a middle of the first thickness.

6. The anatomically shaped implant according to claim 1, wherein the implant is configured for being attached to a bone structure having at least a portion of an edge with a second thickness, wherein the at least one mounting portion is configured such that the extendible portion of the fastener is extendible from the peripheral rim at a middle of the second thickness.

7. The anatomically shaped implant according to claim 1, wherein the channel comprises an enclosed channel portion.

8. The anatomically shaped implant according to claim 1, wherein one side of the peripheral rim is at least one of broader than an other side of the peripheral rim and comprises one or more protrusions extending beyond a periphery of the other side of the peripheral rim, such that, upon placing the implant in the bone defect, the peripheral rim and/or protrusions rest(s) on the edge of the bone defect.

9. The implant according to claim 1, wherein the implant is a cranial implant.

10. The implant according to claim 1, and further comprising one or more markings associated with one or more portions of the implant.

11. A kit of parts comprising:
    at least one of one or more fasteners,
    one or more guides for guiding a cutter,
    one or more cutters,
    one or more tools for operating a fastener, and
    an anatomically shaped implant for attachment to an edge of a bone defect in a bone structure, the implant comprising a curved body and a peripheral rim, the curved body having a curvature at or near the peripheral rim in a direction of extension, wherein the direction of extension at or near the peripheral rim is substantially perpendicular to a tangential direction of the peripheral rim,
    wherein the peripheral rim is configured to be attached to the edge of the defect in the bone structure and comprises at least one mounting portion in a convex portion of an outwardly facing surface of the peripheral rim when the implant is implanted, the at least one mounting portion further having a channel which extends along an axis intersecting the peripheral rim and the axis being oriented at an angle which is at most acute with respect to a surface of the implant and the direction of extension of a central portion of the implant at or near the channel, and wherein the axis extends in a direction substantially perpendicular to the tangential direction at or near the intersection of the axis with the peripheral rim, and is configured to accommodate a fastener attached movable with respect to the at least one mounting portion such that at least a portion of the fastener is extendible through the channel through the peripheral rim,
    wherein the implant is configured such that upon placing the implant in the bone defect, the fastener is arranged in the at least one mounting portion of the peripheral rim movably with respect to the peripheral rim and extendible through the channel into the bone structure in the edge of the bone defect in a controllable manner through the peripheral rim in a direction extending away from the peripheral rim substantially tangential to the curvature.

12. The kit of parts according to claim 11, wherein the at least one mounting portion is configured to receive at least a portion of at least one of the one or more guides for at least one of the one or more cutters for cutting a recess in the edge of the bone defect.

13. The kit of parts according to claim 12, wherein the at least one mounting portion has a first shape and the guide has a shape complementary to the first shape.

14. The kit of parts according to claim 11 wherein the implant has a thickness and wherein the fastener and the at least one mounting portion are configured to define at least one relative position of the fastener and the at least one mounting portion such that one portion of the fastener extends from the implant for extension into the edge of the bone defect and a remaining portion of the fastener is accommodated within the thickness of the implant.

15. A method of attaching an implant in a bone defect in a bone structure, comprising:
    providing an anatomically shaped implant for attachment to an edge of the bone defect, the edge further defining a thickness of the bone structure between an outwardly facing surface and an inwardly facing surface thereof, the implant comprising a central portion and a peripheral rim, and the central portion extending from the peripheral rim in a direction of extension, wherein the direction of extension at or near the peripheral rim is substantially perpendicular to a tangential plane along the peripheral rim, wherein the peripheral rim comprises at least one mounting portion in a convex portion of an outwardly facing surface of the peripheral rim when the implant is implanted
    placing the implant in the defect of the bone structure such that the central portion covers and closes the defect, and
    attaching the peripheral rim to the edge of the bone structure by moving a fastener relative to the implant and in a controlled manner through a channel in the implant along an axis intersecting the peripheral rim in a direction extending away from the peripheral rim at an angle which is zero degrees or acute with respect to the direction of extension of the central portion of the implant and through the edge between the outwardly facing surface and the inwardly facing surface and into the bone structure of the bone defect by moving the fastener along the axis through the peripheral rim in said direction and into the bone structure.

16. The method according to claim 15, wherein at least one of the implant and the bone structure is curved, having a curvature at or near the edge, or the peripheral rim, respectively, and wherein the axis is substantially tangential to said curvature of at least one of the bone structure and the implant, respectively, the fastener extended along the axis, and the central portion of the fastener extended from the implant is accommodated within the bone structure.

17. The method according to claim 16, wherein the curvature has a convex shape.

18. The method according to claim 15, and further comprising:
    determining a first shape of at least a portion of the bone defect and forming at least a portion of the implant with a second shape which is substantially complementary to the first shape.

19. The method according to claim 15, and further comprising:
    wherein the channel extends tangentially to the central portion, the channel configured to accommodate a fastener such that at least a portion of the fastener is extendible through the channel in a direction extending away from the peripheral rim at an angle which is zero degrees or acute with respect to the direction of extension of the central portion of the implant and into the bone structure in the edge of the bone defect,
    providing a guide for a cutter for cutting a recess in the edge of the bone defect,
    arranging at least a portion of the guide in the at least one mounting portion, and
    cutting, guided by the guide, a recess for accommodating at least a portion of the fastener into the edge of the bone defect.

* * * * *

UNITED STATES PATENT AND TRADEMARK OFFICE
CERTIFICATE OF CORRECTION

Page 1 of 1

PATENT NO. : 9,744,042 B2
APPLICATION NO. : 13/497532
DATED : August 29, 2017
INVENTOR(S) : Maikel Michael Adrianus Beerens, Paul Frans Jozef Laeven and Jules Maria Nikolaas Poukens It is certified that error appears in the above-identified patent and that said Letters Patent is hereby corrected as shown below:

On the Title Page

After the Prior Publication Data add:
"(30) Foreign Application Priority Data
Sep. 24, 2009 (EP) .......................... 09171189.5".

Signed and Sealed this
Third Day of July, 2018

Andrei Iancu
*Director of the United States Patent and Trademark Office*